United States Patent
Inwald et al.

(10) Patent No.: US 12,347,538 B2
(45) Date of Patent: *Jul. 1, 2025

(54) SMART MULTIDOSING

(71) Applicant: OptimDosing, LLC, Farmington Hills, MI (US)

(72) Inventors: David Inwald, Berkley, MI (US); Kenneth I. Kohn, West Bloomfield, MI (US); Laura S. Dellal, New York, NY (US)

(73) Assignee: OptimDosing, LLC

( * ) Notice: Subject to any disclaimer, the term of this patent is extended or adjusted under 35 U.S.C. 154(b) by 317 days.

This patent is subject to a terminal disclaimer.

(21) Appl. No.: 16/782,347

(22) Filed: Feb. 5, 2020

(65) Prior Publication Data

US 2020/0245925 A1 Aug. 6, 2020

Related U.S. Application Data

(60) Provisional application No. 62/878,066, filed on Jul. 24, 2019, provisional application No. 62/831,350,
(Continued)

(51) Int. Cl.
*G16H 20/10* (2018.01)
*G06N 5/022* (2023.01)
(Continued)

(52) U.S. Cl.
CPC ............ *G16H 20/10* (2018.01); *G06N 5/022* (2013.01); *G16H 10/20* (2018.01); *G16H 30/20* (2018.01);
(Continued)

(58) Field of Classification Search
CPC ........ G16H 20/10; G16H 10/20; G16H 50/20; G16H 50/70; G16H 70/40; G16H 30/20;
(Continued)

(56) References Cited

U.S. PATENT DOCUMENTS 6,010,492 A 1/2000 Jacobsen et al.
6,658,396 B1 12/2003 Tang et al.
(Continued)

FOREIGN PATENT DOCUMENTS

MX 2013001744 A1 * 6/2013 ............. A61J 3/074

OTHER PUBLICATIONS

Ryu et al., "Deep learning improves prediction of drug-drug and drug-food interactions," PNAS | vol. 115 | No. 18, pp. E4304-E4311 (Year: 2018).*
(Continued)

*Primary Examiner* — Jonathon A. Szumny
(74) *Attorney, Agent, or Firm* — Kohn & Associates PLLC; Kenneth I. Kohn; Laura S. Dellal

(57) ABSTRACT

A method and algorithm for dosing single and multiple drugs for an individual patient includes the step of collecting data from the individual patient. The data includes drugs to be taken by the patient, the patient's age, medical condition, metabolism, and other factors. The method further includes the steps of analyzing the individual patient data in view of dosing criteria established based on patient population data. Based on the analysis, a dose of the single or multiple drugs is recommended. Alternative treatment options can also be recommended.

8 Claims, 4 Drawing Sheets

Related U.S. Application Data filed on Apr. 9, 2019, provisional application No. 62/814,515, filed on Mar. 6, 2019, provisional application No. 62/802,042, filed on Feb. 6, 2019.

(51) Int. Cl.

| | | |
|---|---|---|
| *G16H 10/20* | (2018.01) | |
| *G16H 30/20* | (2018.01) | |
| *G16H 50/20* | (2018.01) | |
| *G16H 50/70* | (2018.01) | |
| *G16H 70/40* | (2018.01) | |

(52) U.S. Cl.
CPC ............. *G16H 50/20* (2018.01); *G16H 50/70* (2018.01); *G16H 70/40* (2018.01)

(58) Field of Classification Search
CPC ........ G16H 10/00–80/00; G06N 5/022; G06N 3/00–99/007; G06F 1/00–2221/2153
See application file for complete search history.

(56) References Cited

U.S. PATENT DOCUMENTS

| | | | | |
|---|---|---|---|---|
| 8,046,242 | B1* | 10/2011 | daCosta | G16H 10/60 600/300 |
| 8,579,856 | B2 | 11/2013 | Sullivan et al. | |
| 8,589,175 | B2 | 11/2013 | Glauser et al. | |
| 9,533,100 | B2 | 1/2017 | Jones | |
| 11,965,206 | B2* | 4/2024 | Stoddard | G16H 10/40 |
| 2001/0001144 | A1* | 5/2001 | Kapp | G16H 20/10 604/131 |
| 2011/0112860 | A1* | 5/2011 | Kehr | G16H 20/10 705/2 |
| 2014/0058350 | A1* | 2/2014 | Stewart | A61M 5/14228 700/282 |
| 2014/0379629 | A1* | 12/2014 | Loew-Baselli | G16B 40/20 706/52 |
| 2018/0060508 | A1* | 3/2018 | Fokoue-Nkoutche | G16H 15/00 |
| 2019/0325249 | A1* | 10/2019 | Tahmasebi Maraghoosh | G06T 17/10 |
| 2020/0234810 | A1* | 7/2020 | Athey | G16B 30/00 |
| 2021/0065859 | A1* | 3/2021 | McKinney | G16H 30/40 |

OTHER PUBLICATIONS

Cheng et al., "Machine learning-based prediction of drug-drug interactions by integrating drug phenotypic, therapeutic, chemical, and genomic properties," J Am Med Inform Assoc 2014;21:e278-e286. (Year: 2014).*

Nemati et al., "Optimal Medication Dosing from Suboptimal Clinical Examples: A Deep Reinforcement Learning Approach," Annu Int Conf IEEE Eng Med Biol Soc. Aug. 2016; 2016:2978-2981 (Year: 2016).*

Abacha et al., "Text mining for pharmacovigilance: Using machine learning for drug name recognition and drug-drug interaction extraction and classification," Journal of Biomedical Informatics 58 (2015) 122-13 (Year: 2015).*

Gottlieb et al., "INDI: a computational framework for inferring drug interactions and their associated recommendations," Molecular Systems Biology 8; Article No. 592; doi:10.1038/msb.2012.26. (Year: 2012).*

* cited by examiner

SMART MULTIDOSING

BACKGROUND OF THE INVENTION

1. Technical Field

The present invention relates to methods of determining dosing of single and multiple drugs for patients. More specifically, the present invention relates to methods, software, and algorithms for determining safe and efficacious single and multiple drug doses for an individual patient or a patient population based on compilation and analysis of clinical data.

2. Background Art

Many individuals, especially as they age, need to take multiple drugs for different indications. Taking multiple drugs comes with risks, because drug interactions can cause unwanted and harmful side effects, and even cognitive side effects that can impact daily activities. In the time period of 2011-2014, the CDC states that 23.1% of individuals used three or more prescription drugs in the past 30 days, and 11.9% used five or more prescription drugs in the past 30 days. Over 40% of individuals over 65 years old are taking five or more drugs daily. Many individuals who also decide on an appropriate dose for themselves (such as increasing a dose) without doctor input can also inadvertently cause a reaction with other drugs that they self-administer. Even doctors may not be aware of drug interactions, and tools for pharmacists are limited to producing a warning if a combination is explicitly counter-indicated. Aside from strict counter-indicators, it is up to the individual to ask a pharmacist of any potential problems. Many individuals also take over-the-counter drugs, vitamins, and supplements without thinking that they may have an impact on each other and/or on prescription drugs.

Quinn, et al. (Sci. Data. 2017; 4: 170167) states that half of patients taking prescription drugs are taking two or more, and 5% take eight or more, and most multidrug combinations are used for treating metabolic syndrome. Quinn, et al. studied insurance claims to determine the number of prescription drugs patients are taking within a 30 day window that overlap. Table 3 in Quinn, et al. details the 3-drug combinations that are most represented prior to emergency department visits. Table 4 details the most common and overrepresented drug ingredient co-exposures with metformin or oxycodone.

Online drug interaction checkers exist, such as Drugs.com, and websites like these can provide warnings of interactions with a drug that an individual is taking. A list of side effects is generated for each combination of drugs. However, there is no information as to whether a particular dose causes an effect, or what dose the individual should take based on the combination of drugs that the individual is already taking.

With the continued advancement and expansion of pharmacogenetics testing into clinical practice, the widespread adoption of electronic health record (EHR) systems in hospitals and other clinical research centers, and the development of PKPD models to guide, model-informed dosing, there has been progress toward what is termed precision medicine. However, significant technical and logistical challenges remain to be addressed. "Precision dosing" has been defined as the optimization of drug dosing in individual patients with the goal of maximizing efficacy and/or minimizing toxicity. In the area of precision dosing, DoseMeRx and InsightRx provide software that leverages clinically validated pharmacokinetic drug models, patient characteristics, drug concentrations and genotype to suggest dosing of drugs. Both use Bayesian statistical models to predict a particular patient's response to dosing method variations.

U.S. Pat. No. 6,658,396 to Tang, et al. discloses neural networks that are trained on historical data, and used to predict any of (1) optimal patient dosage of a single drug, (2) optimal patient dosage of one drug in respect of the patient's concurrent usage of another drug, (3a) optimal patient drug dosage in respect of diverse patient characteristics, (3b) sensitivity of recommended patient drug dosage to the patient characteristics, (4a) expected outcome versus patient drug dosage, (4b) sensitivity of the expected outcome to variant drug dosage(s), (5) expected outcome(s) from drug dosage(s) other than the projected optimal dosage. Both human and economic costs of both optimal and sub-optimal drug therapies may be extrapolated from the exercise of various optimized and trained neural networks. Heretofore little recognized sensitivities—such as, for example, patient race in the administration of psychotropic drugs—are made manifest. Individual prescribing physicians employing deviant patterns of drug therapy may be recognized. Although not intended to prescribe drugs, nor even to set prescription drug dosage, the neural networks are very sophisticated and authoritative "helps" to physicians, and to physician reviewers, in answering "what if" questions. However, Tang, et al. cannot analyze multiple drugs in combination. Further, the neural network approach described has inherent limitations when applied to the simultaneous dosing of multiple drugs. More specifically, the amount of contextual data needed to make an informed decision using a neural network as described is not currently available.

Therefore, there remains a need for an effective method of managing multiple drugs and suggesting appropriate doses based on the combination of drugs being taken.

SUMMARY OF THE INVENTION

The present invention provides for an algorithm and method for dosing single and multiple drugs, by collecting patient data including drugs to be taken by the patient, analyzing the patient data in view of dosing criteria established based on outside patient data (population data) wherein patients experienced safety and efficacy, and determining a dose or doses of the single or multiple drugs, respectively, for each drug taken.

The present invention further provides for a logic engine for dosing multiple drugs, including an algorithm stored on non-transitory computer readable media for collecting outside data to establish criteria for safely and efficaciously dosing multiple drugs to a single patient and patient data and storing the outside data and patient data in a database, best fitting the patient data into the outside data matching dosing of the drugs or drugs to the safety and efficacy dosing in the outside data, and determining a dose or doses of the single or multiple drugs, respectively, for each drug taken.

DESCRIPTION OF THE DRAWINGS

Other advantages of the present invention are readily appreciated as the same becomes better understood by reference to the following detailed description when considered in connection with the accompanying drawings wherein.

DETAILED DESCRIPTION OF THE INVENTION

Figure 1:
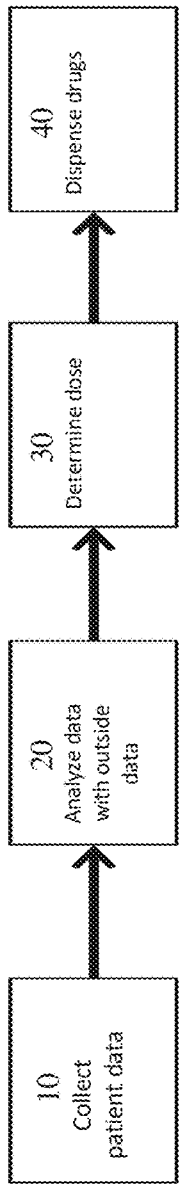
FIG. 1 is a sequential schematic of the method of the present invention.

The present invention generally provides for methods of dosing multiple drugs when taken together to ensure that patients receive a safe and effective dose of each drug. Most generally, as shown in FIG. 1, the method includes collecting patient data 10 from an individual patient with proposed treatment plan details including drugs to be taken, patient age, sex, disease state, metabolism, enzyme levels, and other pertinent patient health information, including genetic information, analyzing the present patient's data in context of outside data (population data) 20, and determining a safe and efficacious dose for each drug with output data 30. The dose determination is an optimization of maximizing therapeutic effect (efficacy) while minimizing likelihood of adverse effects (safety) for the combination of drugs to be taken. This considers data relating to pharmacokinetics, distribution, prior toxicity and efficacy determinations, age, metabolism, side effect predictions, and any other criteria related to toxicity and efficacy outcomes. In other words, known data, referred to above as outside data, is compiled from prior drug data studies (Phase 1 through Phase 4 trials) as well as data sources from hospitals, health centers, clinics, etc. is used to train a data model that is then adapted to specific data from an individual patient to be treated in order to predict proper safe and efficacious dosing of multiple drugs for the individual patient. The method can further include dispensing the drugs to the patient in the prescribed dose 40. The method would then be used in a closed system wherein patient data could be continually collected and entered and analyzed. In real time, a dispensing device is controlled to adjust dosing and administration based on the real time changes in the patient's condition. In the case of dispensing, the present invention ensures sufficient evaluation criteria was provided before suggesting an outcome. The present invention further provides for a logic engine (i.e. a computer program) for performing the method, including an algorithm stored on non-transitory computer readable media for collecting patient data 10 and storing the patient data in a database 50, analyzing the patient data in view of outside data 20, and determining a dose for each drug with output data 30.

Most generally, the flow of information used in the present invention is Data Input→Central AI↔Healthcare Professional. The data input can be from, but is not limited to, clinics, electronic medical records (EMRs), pharmaceutical companies, private databases, or CROs. The healthcare professional can be, but is not limited to, an MD, pharmacist, hospital, insurer, nurse, laboratory professional, or other medical professional. The healthcare professional can then input data regarding the patient back into the central AI such as, but not limited to, patient data from monitors (including at a medical facility and personal monitors such as smart devices), data from EMRs, insurance information. Any of the data being collected and received can be in real time. From the data input to the central AI, the AI creates complex relationships between any and all variables that effect drug metabolism, with capability to relate how these variables are affected by dosing of additional consumed drugs.

The AI applies a pre-trained model to a patient's specific physiology, metabolism, etc. for drugs being taken. As these factors can be induced to change by a change in disease state, drug induced changes, etc., real time monitoring of these changes can assist in real time drug dosing adjustments. While such a system may not be practical for all home care, but is practical for patients already on monitors and mechanically/digitally receiving drugs.

The system is both patient and drug centric. The AI creates a model relating dosing to patient condition and effect of other drugs on that condition which effect efficacy of all drugs taken and toxicity of all drugs taken. The AI identifies complicated multivariable relationships while producing simple clinical outputs of recommended dosing range of the multiple drugs (as well as specific instructions, warnings, or otherwise important information), or actually in real time administer those drugs. The features considered in the model can be, but are not limited to, age of patient, weight of patient, known side effects of drugs alone and in combinations with other drugs, known toxicity range as related to ED 50 and other dose response points of interest, efficacy ranges, and chronic treatment effect versus acute treatment (one time dosing versus dosing over time). Such factors can be gathered from clinical studies along with other information as necessary and then the patient can be fit into matrix to determine dosing for drugs needed.

Figure 2:
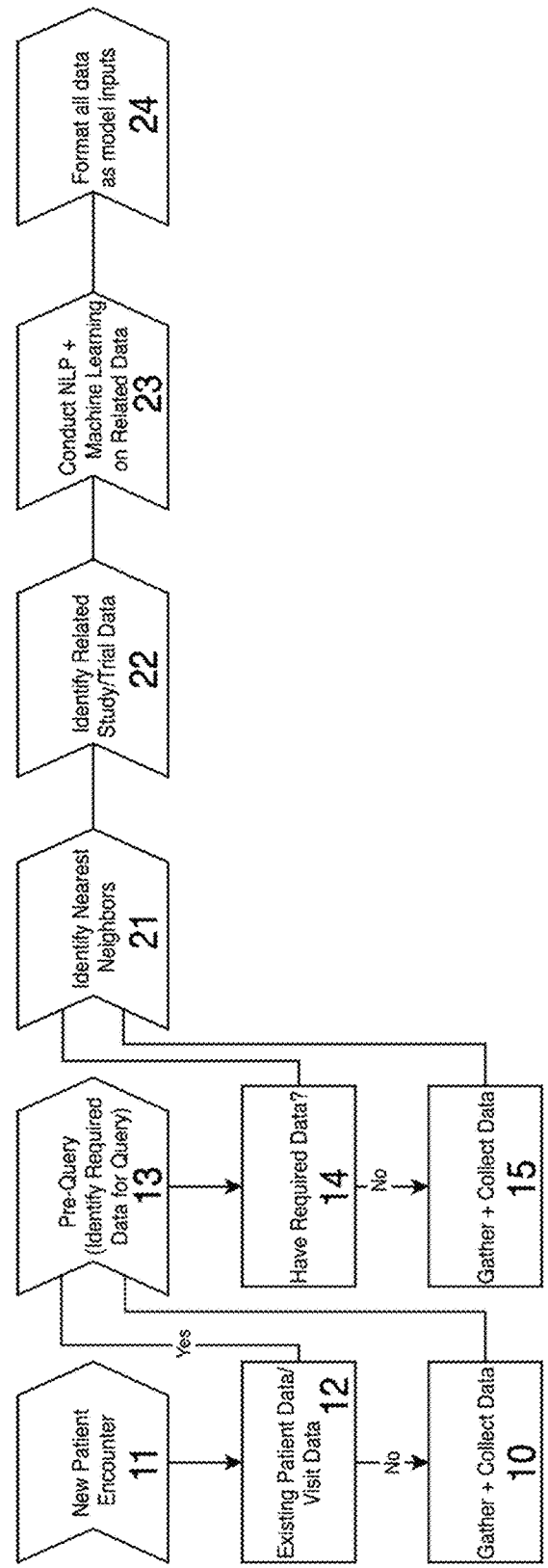
FIG. 2 is a schematic of the method the present invention uses to prepare and condition input data.
Figure 4:
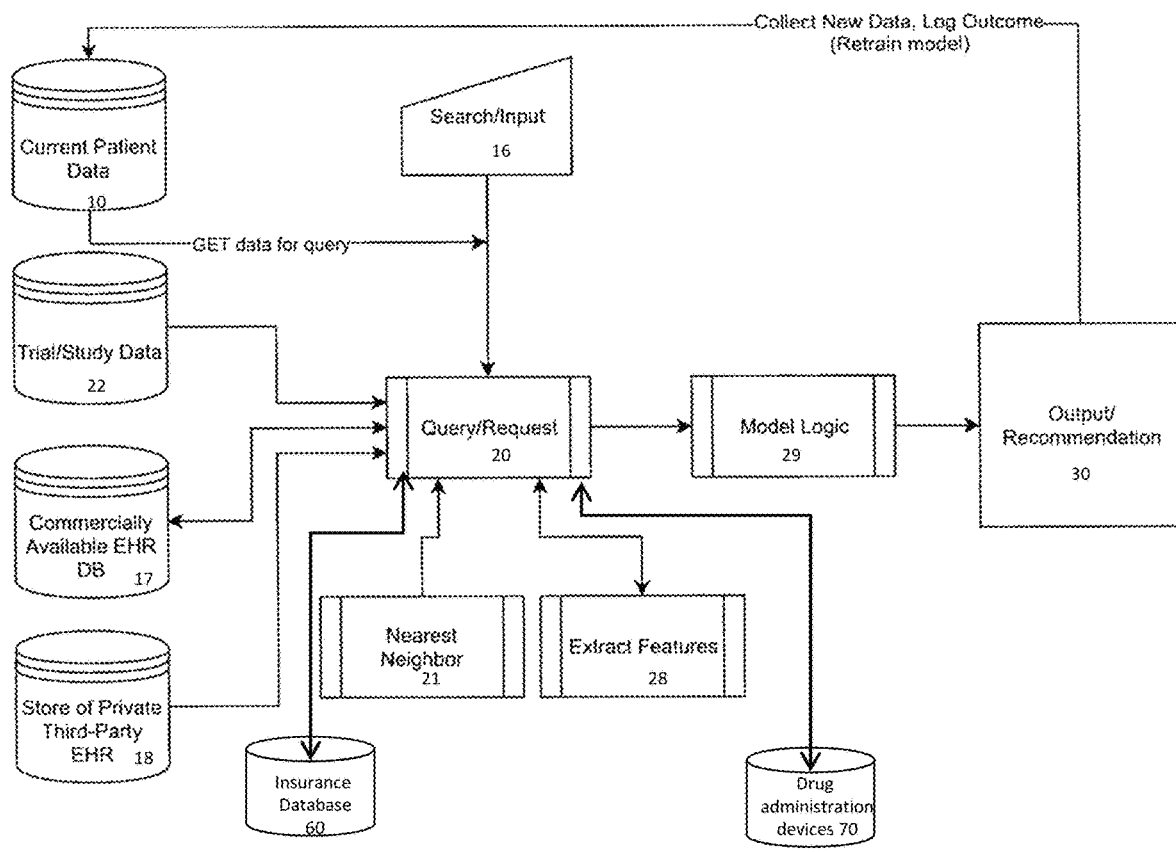
FIG. 4 is a schematic of the method of the present invention.

The method and logic engine are shown in greater detail in FIGS. 2 and 4. At a patient encounter 11, it is first determined if there is any existing fit history or visit data 12. If not, patient data can be collected 10 as detailed below. A pre-query 13 is performed to identify any required data points to perform an analysis. Data can be gathered directly from a patient file of an electronic health record into which the present invention is incorporated or otherwise in communication with, such as a plug in into the electronic health record. This includes checking whether particular lab values are needed before an optimized dose can be predicted. If the required data points 14 are not present, then they are gathered or collected 15. Next, the nearest neighbors are identified 21, representing a set of patient data most similar to the present patient. Then, related study/trial data is identified 22, Natural Language Processing (NLP) is conducted on related unstructured data 23, before being conditioned as inputs/features for the model 24. Natural Language Processing is a type of AI that extracts features from unstructured text, such as, but not limited to, patient notes or items appearing in string-type text fields in drug trials. The unstructured data can also include additional side effects, or notes from any questioning otherwise not expressed in a structured data field.

Various data is collected about the patient 10 and entered into a database 50 on computer readable media. This includes symptoms, diagnoses, and proposed drugs/treatments 16 that the patient has been prescribed to take by a doctor or other medical professional. More specific data can be collected from analysis of blood and urine samples related infectious disease, metabolism, presence of antigen indicated disease (such as cancer, MS, etc.), patient temperature, blood pressure and other data routinely or additionally collected by the health care professional or present in the patient's electronic health record.

Fixed demographics can be collected, such as, but not limited to, age, gender, race, height, known drug interactions, and body composition (fat, muscle content). All of these criteria, including genetic inclination to drug metabolism and general metabolism, resistance and susceptibility to disease, and other related criteria are analyzed, as each can be individually pertinent related to the metabolism of each individual drug prescribed and taken by the patient, as well as the combined effects of each of the drugs on each other. In other words, consideration is taken into account regarding the drugs individual effects on the patient as well as the effects of the combined combination of drugs being taken.

Temporal values can be collected, such as, but not limited to, historic values from existing electronic medical records (EMR) or electronic health records (EHR), current/up to date values, cholesterol, blood pressure, weight, and diagnostics related to a specific ongoing disease. The database 50 can be in electrical connection with commercially available EHR databases 17 and private third-party EHR databases 18 to search for relevant data and extract data to the database 50 for analysis. Patient data related to diet (i.e. specific foods eaten often, especially ones known to have interactions with drugs) and nutritional supplements can also be collected, as well as exercise habits. Information can be self-reported or collected from wearable devices, in-home data sensors, etc.

Genetic components can be collected, such as, but not limited to, key genetic markers, whole genome data from genetic testing/ancestry sites, or test results from any type of genetic tests. Genetic components are important not just for markers for known drug efficacy, but also for generating ethnicity and demographics features for multidimensional nearest neighbor calculations (further described below). Genetic components can be analyzed not only to determine an optimized dose, but also to potentially avoid higher risk factors for adverse symptoms. The known effects of drugs on liver enzymes, critical to first pass drug metabolism will be considered and analyzed as each drug alone and in combination effects the liver enzymes differently. So the capacity of the patient's liver enzymes as well as the drug effect on the liver enzymes are synthesized in the analysis.

Various imaging can be collected, such as, but not limited to, CAT scans, CT scans, X-rays, MRI, ultrasounds, PET scans, or other visual analyses. Reports from imaging studies are analyzed and encoded using an NLP algorithm to extract features. These features, along with structured findings from a radiologist are used to inform the model.

Unstructured data can also be collected, such as, but not limited to, any patient notes over time. Natural language can be processed into a network of classifiers to identify propensities for certain risk factors, given certain patient notes. For example, there may be a correlation between the presence of hygiene concerns in a patient note and reduced likelihood of adherence to a drug therapy regime. Unstructured patient data includes notes by healthcare professionals as well as information collected directly from the patient including responses questionnaires, intake forms, etc.

This patient data structure, when fully populated, contains the full digital footprint needed to make queries into the logic engine. Instead of a fixed patient data structure, the patient model is fluid and its makeup of fields is determined by the desired outcome of the model. This reflects the fluidity of the patient's stasis as the patient's condition ultimately requiring the need for multiple drug consumption and the related dosing is fluid as the patient initially succumbs to a disease, is treated with the drugs, and then hopefully recovers from the disease. As the patient's stasis changes and hopefully returns to homeostasis, dosing can be altered.

The logic engine can request supplemental data 13 based on the patient data. Once trained, the logic engine has the ability to apply a discrete weighting regime to extracted features 28 based on their significance, i.e. request a blood level or demographic data point prior to making a dosing recommendation, imaging, pharmacogenomics testing, lifestyle questions, or any other type of diagnostics required. Different drug combinations will require different sets of supplemental data. Additional data selection can be weighted by importance, invasiveness, cost, and availability. For example, if a certain test is not available or prohibitively invasive, the logic engine reacts accordingly by being transparent with the decreased accuracy or exposure to potential risk.

Since the required input data varies on numerous conditions, essential data points are unknown until the basic query has started. If no further data is needed, the logic of the present invention can continue without additional input. Also, data can be weighted and combinations of data can be weighted.

Figure 5:
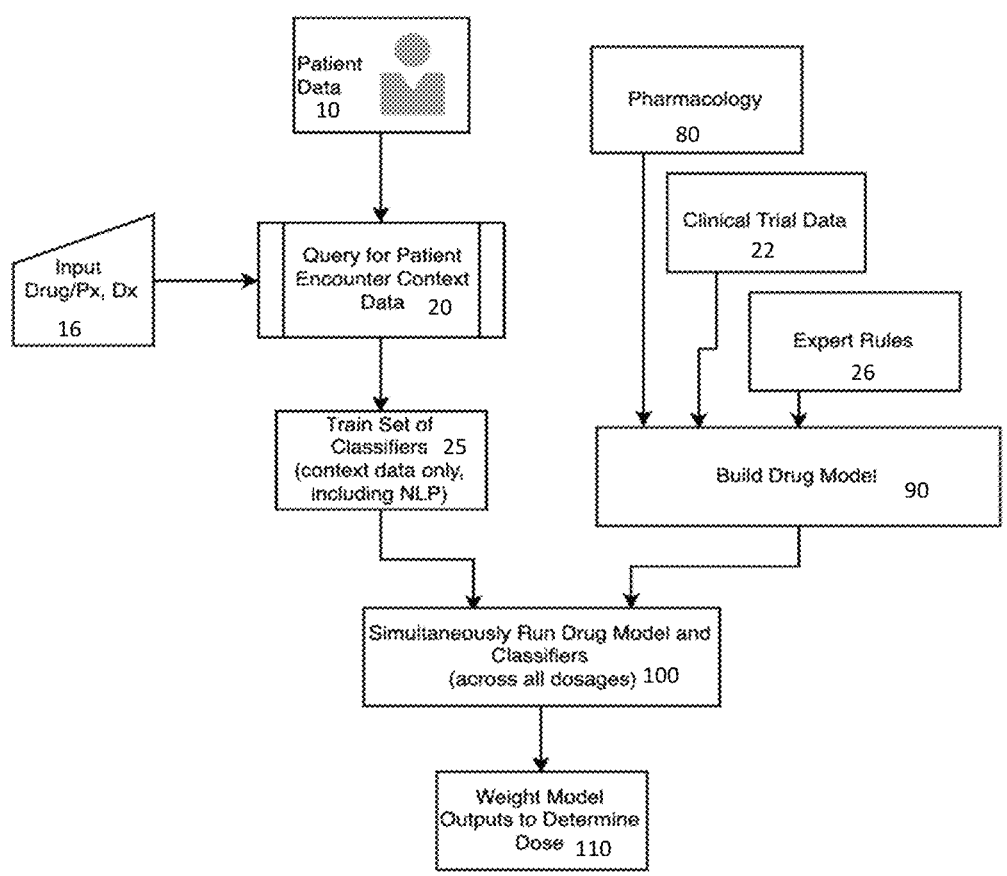
FIG. 5 is a schematic of the method of the present invention.

The database 50 can also collect information relating to the drugs desired to be prescribed (i.e. pharmacology information 80, shown in FIG. 5). Pharmacology information 80 can include drug mechanism of action, the safe dosage range, the suggested dosing strategy, and other pharmacological properties such as liberation, absorption, distribution, metabolism, and excretion. These factors and any other available information are taken into consideration to develop the drug-based model.

Pharmacology information 80 can include information from animal studies that can be used for initial dosing in humans. This can particularly be useful in designing FDA drug trials and especially for INDs. For example, allometric scaling can be performed wherein the dose in an animal is normalized based on body surface area to humans (FDA Guidance for Industry, Estimating the Maximum Safe Starting Dose in Initial Clinical Trials for Therapeutics in Adult Healthy Volunteers; Nair, et al. Journal of Basic and Clinical Pharmacy, 2016). Allometric scaling can be useful in drugs having lesser hepatic metabolism, low volume of distribution, and are excreted by renal route. Scaling based on weight can also be used. Other methods may need to be used for the following drugs according to the FDA. 1. Therapeutics administered by alternative routes (e.g., topical, intranasal, subcutaneous, intramuscular) for which the dose is limited by local toxicities. Such therapeutics should be normalized to concentration (e.g., mg/area of application) or amount of drug (mg) at the application site. 2. Therapeutics administered into anatomical compartments that have little subsequent distribution outside of the compartment. Examples are intrathecal, intravesical, intraocular, or intrapleural administration. Such therapeutics should be normalized between species according to the compartmental volumes and concentrations of the therapeutic. 3. Proteins administered intravascularly with Mr>100,000 daltons. Such therapeutics should be normalized to mg/kg.

Human equivalent dose (HED) from an animal dose can be determined if the animal no observed adverse effect level (NOAEL) is known. The NOAEL is the highest dose level that does not produce a significant increase in adverse effects in comparison to the control group. The equation below uses a correction factor for body surface area.

$$\text{HED(mg/kg)} = \text{Animal NOAEL(mg/kg)} \times (\text{weight}_{animal}[kg]/\text{weight}_{human}[kg])^{(1-0.67)}$$

Table 1 shows conversion factors for interspecies dose conversions for NOAELs.

TABLE 1

Conversion of Animal Doses to Human Equivalent Doses Based on Body Surface Area

| Species | To Convert Animal Dose in mg/kg to Dose in mg/m2, Multiply by km | To Convert Animal Dose in mg/kg to HEDa in mg/kg, Either: Divide Animal Dose By | To Convert Animal Dose in mg/kg to HEDa in mg/kg, Either: Multiply Animal Dose By |
|---|---|---|---|
| Human[a] | 37 | — | — |
| Child (20 kg)[b] | 25 | — | — |
| Mouse | 3 | 12.3 | 0.08 |
| Hamster | 5 | 7.4 | 0.13 |
| Rat[c] | 6 | 6.2 | 0.16 |
| Ferret | 7 | 5.3 | 0.19 |
| Guinea pig | 8 | 4.6 | 0.22 |
| Rabbit | 12 | 3.1 | 0.32 |
| Dog | 20 | 1.8 | 0.54 |
| Primates: | | | |
| Monkeys[c] | 12 | 3.1 | 0.32 |
| Marmoset | 6 | 6.2 | 0.16 |
| Squirrel monkey | 7 | 5.3 | 0.19 |
| Baboon | 20 | 1.8 | 0.54 |
| Micro-pig | 27 | 1.4 | 0.73 |
| Mini-pig | 35 | 1.1 | 0.95 |

[a]Assumes 60 kg human. For species not listed or for weights outside the standard ranges, HED can be calculated from the following formula: HED = animal dose in mg/kg × (animal weight in kg/human weight in kg)0.33.
[b]This km value is provided for reference only since healthy children will rarely be volunteers for phase 1 trials.
[c]For example, cynomolgus, rhesus, and stumptail.

A safety factor can also be applied to the HED to provide a margin of safety for humans. Generally, a safety factor of 10 is used, but this can be adjusted based on different circumstances (raised when there is reason for increased concern, lowered when concern is reduced because of available data that provide added assurance of safety).

Parenteral administration doses can be calculated from the following equation. The results can be checked against FDA maximum injection volume guidelines.

Injection volume(mL)=animal weight(kg)×animal dose(mg/kg)/concentration(mg/mL)

Prescriptions of certain drugs (or combinations of drugs) can require pharmacogenomic testing to check for certain markers. These markers can help decide between different classes of drug, circumvent known risk factors, as well as optimize the dosages. Since the effectiveness of a therapy is influence by the presence of certain markers, the results from genetic testing can be critical inputs. Pharmacogenomic testing is widely used when evaluating medications used in the treatment of ADD/ADHD and depression, anticoagulants, and others. The use and availability of data from pharmacogenomic testing is on the rise due to decreasing costs.

Mimicking the human expert decision making process, all data pertinent to making an informed decision must be made available and formatted prior to running the logic engine. The logic engine can proceed with missing data points, however, accuracy and therefore confidence in the decision are reduced.

Data from Nearest Neighbors data can be identified 21. A key aspect to the success of the present invention is the use of contextual data from similar patients. A "nearest neighbor", as used herein, can be persons that have similar patient data and/or underwent a treatment plan with similar drug combinations. Identifying existing records similar to the patient in treatment is a key component to the accuracy of the logic engine. A multi-dimensional nearest neighbor algorithm is used to find those individuals from existing sets, i.e. a K-Nearest Neighbor (K-NN) algorithm. The K-NN algorithm is a clustering algorithm and acts as a non-parametric untrained classifier that evaluates the overall similarity between two patients/subjects based on the degree of differences across multiple features. The flexibility of such an algorithm allows consideration of many parameters when searching for pertinent context data. Weights on certain factors vary depending on the type of diagnosis and class(es) of drug(s) being prescribed. For example, a specific patient might be more willing to risk side effects in exchange for efficacy. The set of similar patient profiles are grouped into subsets to look for trends that can be used to optimize the treatment plan of the given patient. While the K-NN algorithm can be preferred, other clustering algorithms can also be used, such as, but not limited to, K-Means, Affinity Propagation, Mean Shift, Spectral Clustering, Support Vector Machines. One advantage of K-NN over other techniques is that it is easily scalable across many dimensions-meaning additional features can easily be considered without having to restructure the logic of the algorithm. Further, from case-to-case the differing dimensions and weights are easily included.

The purpose of the K-NN algorithm is to find patients most similar to the present patient. Once identified, the "neighboring" patient data, including treatment plan and outcome, are used to evaluate the present subject. To make the identification, we evaluate the differences in each parameter comprising the patient data structure. While most commonly used with continuous values (weight, age, LDL level, etc.), the algorithm can be used with discrete values as well (race/ethnicity, familial history, presence of certain symptoms, etc.). The differences across each parameter are combined using a weighting scheme such that a normalized 'distance' is produced representing an overall difference metric between two patients. The distance calculation between two patients is achieved using a regression-type K-NN algorithm. Key to the regression evaluations is the Mahalanobis distance. The Mahalanobis distance evaluates to a Euclidian distance since the covariance matrix is always the identity matrix, i.e., one parameter in this case is never to be compared independently with another parameter. The benefit of adapting the Mahalanobis distance instead of using pure Euclidian distance is that Mahalanobis distance includes the measurement of the number of deviations away from the norm. While the actual standard deviation is not always ideal, an equivalent term is used.

If the present patient $P_1$ has a set of parameters where $P_1=\{\mu_{1Pa}, \mu_{2P1}, \mu_{3P1}, \ldots \mu_{NP1}\}$ and an arbitrary patient, $P_\beta$, where $P_\beta=\{\mu_{1P\beta}, \mu_{2P\beta}, \mu_{3P\beta}, \ldots \mu_{NP\beta}\}$, then the distance, D, between the two patients is:

$$D_1(P_1,P_\beta)=\sqrt{\Sigma_{i=1}^{N}(\mu_{iP1}-\mu_{iP\beta})^2}$$

Several adaptations are needed to the above generalized equation. Mainly, handling a weighting schema. Most simply, a set of weights, W, should be created with each parameter in P being assigned a weight. Weights can be applied using any technique. Shown below is an intuitive 1-10 linear weighting schema. If $W=\{\rho_1, \rho_2, \rho_3, \ldots \Sigma_N\}$ then the distance, D, can be evaluated by:

$$D_2(P_1,P_\beta)=\sqrt{\Sigma_{i=1}^{N}\rho_i(\mu_{iP1}-\mu_{iP\beta})^2}$$

In the above examples for $D_1$ and $D_2$ continuous values are used for $\mu_N$. In this application, continuous values can be integers or rational numbers. Discrete values must be handled in a special manner. Since there is no intuitive value for the difference between two ethnicities, one must be manually supplied in a lookup table. Algorithmically, parameters with continuous values should be summated using the squared difference while parameters with continuous values are summated manually. The same $W=\{\rho_1, \rho_2, \rho_3, \ldots \rho_N\}$ weighting schema applies to discrete parameters as well.

The threshold for evaluating whether or not another patient is sufficiently similar to the present patient is situational. The ideal number of similar subjects is to be optimized on a case-to-case basis when there exists sufficient training data.

K-NN algorithms have been used before. For example, U.S. Pat. No. 10,123,748 (IBM) discloses a Patient Risk Analysis method that uses K-NN to find similar patients. U.S. Pat. No. 7,730,063 discloses a personalized medicine method that also mentions K-NN as a potential algorithm for finding similar patients. The present invention's ability to include continuous and discrete parameters as well as customized weights in the K-NN differentiates over these prior art methods.

The inputs to the logic engine are broad and complex. AI techniques such as the K-NN algorithm are applied to the inputs to precondition the data. By taking this step to precondition data, the following processing steps are simplified.

The logic engine employs a combination of artificial intelligence techniques, both supervised and unsupervised. Instead of using a broad-scale program that is trained once, the logic engine in the present invention is unique to the inputs and is therefore trained on demand. The benefit to this technique is to emphasize the individuality of the patient and the symptoms.

Figure 3:
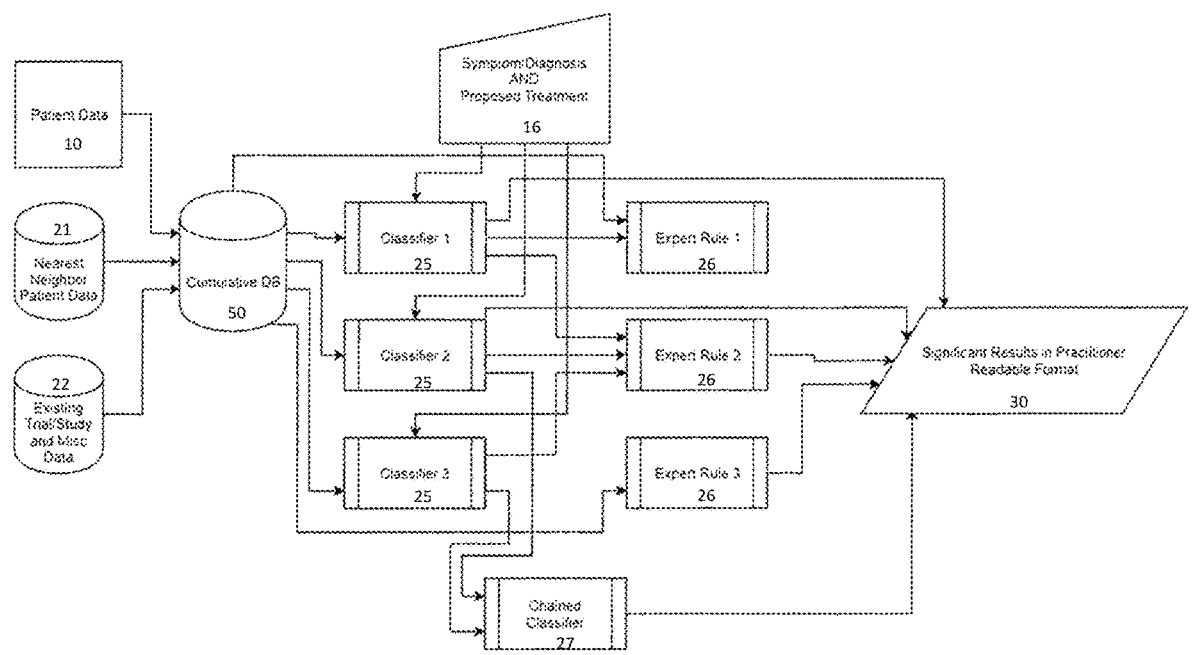
FIG. 3 is an example schematic of applied classifiers and expert rules in the method.

Most broadly, and as shown in FIG. 3, the present invention includes model logic 29 composed of a series of classifiers 25, some of which offer direct outputs (such as the likelihood for an occurrence of a direct drug interaction or the presence of a certain side effect), while others perform intermediary steps. Classifiers 25 and expert rules 26 implemented in series is a strategy known as chaining 27, a process that takes advantage of the smaller preprocessing steps conducted by earlier-staged processing. Processing data using classifiers 25 in this way codes the patient information into a format suitable for use in existing artificial intelligence techniques. Most commonly, this involves assigning a quantitative element to inherently non-quantitative data. Data points, such as the presence of a side effect, are turned into features. Data elements can be Boolean or continuous depending on the type. Each individual data element is assigned a confidence and a weight. The confidence is a representation of the accuracy of the element, while the weight represents the importance.

The expert system also contains a series of rules 26 prepopulated by practitioners and otherwise published research. These rules 26 can be drug or drug-class specific and compose the supervised learning aspect of the AI. In the spirit of fuzzy logic systems, each rule 26 is assigned a varying degree of truth, establishing a crude weighting scheme.

The classifiers 25 and the drug model 90 are ran simultaneously across all possible dosage ranges 100. For each dosage, classifications with confidence intervals are calculated. The generic drug model is ran using the same set of dosages mapped out to the same classifiers used when evaluating context data. The outputs from both models are weighted and combined to determine the optimal dose 110 in the output 30.

A major differentiator with the present invention relates to the mimicked expert output 30 of the logic engine. The output of the logic engine is an overall comprehensive analysis of the present patient, the diagnosis, and the primary method of treatment with dosages for each diagnosis. Any notable findings related to drug interaction, decreased efficacy, or side effect management are incorporated into the output. In this way, the full treatment plan is considered rather than the industry status quo of evaluating the possibility of toxicity or otherwise adverse reaction for specific drug combinations. It accomplishes producing an output based on data not accessible by the practitioner or pharmacist. Analysis is provided to determine output presently not considered by the practitioner. Presently, the only assistance to the practitioner or pharmacist is in the nature of do or do not do. That is, do give certain drugs together or do not based on general know toxicities. Nothing is available that assists in not only minimizing toxicity, but also maximizing efficacy of drug combinations.

The format of the output 30 can be a practitioner readable report with information being displayed in a manner to easily allow the user to identify categories of alerts. Certain outputs 30 can alter the course of a treatment altogether while other times an output might reinforce a direction in an attempt to mitigate an already known side effect. When applicable, the likelihood or confidence approximation is presented as well. This transparent output 30 format is all in an attempt to synthesize relative information when the practitioner is facing a treatment decision.

The output 30 can also be sent to a pharmacy or self-dispensing machine where the determined dose of each drug can be prepared for the patient 40. The output 30 can also provide the patient with instructions of how to take each drug and side effects to watch out for, as well as contraindications with commonly taken over the counter medications, supplements, and food. The output 30 can be sent wirelessly to any medical professional or the patient to read on a mobile device, tablet, laptop, or desktop computer. While doctors can use the logic engine to initially prescribe drugs at a certain dose to a patient, the logic engine can also be used by pharmacists to check a doctor's prescription in view of the other drugs that the patient is currently taking to make sure that the dose is correct and to reduce side effects.

The database 50 can further be in electronic communication with an insurance company's databases 60 and have access to a particular patient's insurance plan. Once a particular dose of the drug combination has been determined, the logic engine can further analyze the cost feasibility of the patient taking the particular combination of drugs according to what their insurance will cover. The logic engine can determine costs for the patient and determine if a generic drug is available for a particular input drug, or if a similar working drug that costs less is available. If a similar lower-cost drug is available, the logic engine can provide optimal dosing for that drug as a substitute as well as any information regarding side effects or efficacy as compared to the original input drug.

The database 50 can also be in electronic communication with drug administration devices 70. This can be to the extent of real time dosing, administration, patient data gathering, and dosing adjustment based on the real time data. In other words, after running the logic engine, and based on the recommended doses of drugs taken by the patient, the drug administration device 70 can receive updated dose information and adjust future doses accordingly. Electronic communication can be wireless or wired (such as with BLUETOOTH® or downloadable with a USB connection) and signals can be sent at the time that a dose is administered. These devices can include, but are not limited to, transdermal patches, intravenous drips, self-injection and auto-injection devices, wearable injection devices, and implantable drug delivery devices.

The present invention has several advantages over the prior art. Many current pharmacology related software checks for known high-level interactions between two specific drugs or drug classes. Going beyond that simple check, the present invention checks nearest neighbor patient outcomes when given similar drug combinations. Even if there is no indicated complication, a decrease in efficacy or increase in side effects are identified in order to be avoided.

Further, outputs of the algorithm are never limited to an amount of active ingredient, instead, full treatment plans are suggested. This information can be relayed to the patient or used internally for the decision making process. Therefore, the present invention provides a technical effect of providing a treatment plan with dosing of particular drugs to the patient, as well as providing to the patient the recommended doses. There is potential to maximize predicted efficacy of a treatment plan while acting in accordance with the labeled use of the drug. Varying treatment plans can be justified if trends suggest preferred outcomes for similar patient profiles. Instead of the present invention being treated as a dosage calculator, it is more so a decision making tool that expertly considers all necessary information to make more informed treatment plans.

The present invention provides advantages to patients because instead of being prescribed drug combinations at sub optimal and sometimes sub efficacious levels to avoid toxicity and then being dosed up to efficacy while hopefully avoiding toxicity, the present invention can initially dose single or multiple drugs to a patient at nontoxic and efficacious doses. Thereby, the patient is immediately treated (critical in acute situations such as stroke, seizures, arrhythmia, etc), while avoiding toxicity.

The present invention provides advantages to physicians because they no longer have to guess at dosing, especially in situations of prescribing multiple interacting drugs. The platform also takes into account the patient's clinical and physical conditions thereby personalizing the patient's prescription.

The present invention provides advantages to pharmaceutical companies due to avoidance of adverse effects related to either drugs toxicity or apparent inefficacious use of recommended therapeutics. There are also drug development benefits. The platform can be used to analyze early clinical study data to define a preferred study class for a Phase 3 study. The risk of study failure is greatly reduced.

The present invention provides advantages to insurers by decreasing potential malpractice cases against physicians based on alleged improper prescription practices. Pharmaceutical companies will benefit for the same reasons. More important is that drugs, especially in multi-prescription situations, can be prescribed to more efficiently be efficacious. Many drugs are underdosed by physicians afraid of toxicity issues, especially in chronic dosing situations. This results in false negative results and patient failure. Insurance providers are unjustly penalized under those situations. The added cost of the implementation of the platform will be greatly outweighed by the financial benefit and practical benefit to the patient. This removes sometimes unjust prejudice to the pharma brand, adding value to the pharma industry.

The present invention can be useful in dosing any combination of drugs. The drugs can be generally from the classes antihistamines, anti-infective agents, antineoplastic agents, autonomic drugs, blood derivatives, blood formation agents, coagulation agents, thrombosis agents, cardiovascular drugs, cellular therapy, central nervous system agents, contraceptives, dental agents, diagnostic agents, disinfectants, electrolytic, caloric, and water balance, enzymes, respiratory tract agents, eye, ear, nose, and throat preparations, gold compounds, heavy metal antagonists, hormones and synthetic substitutes, oxytocics, radioactive agents, serums, toxoids, and vaccines, skin and mucous membrane agents, smooth muscle relaxants, and vitamins. Some specific combinations of drugs that are most commonly used by people include, but are not limited to, lisinopril and atorvastatin, lisinopril and metformin, amlodipine and lisinopril, alprazolam and amphetamine salt combo, amphetamine salt combo and amphetamine salt combo xr, hydrocodone/acetaminophen and alprazolam, amlodipine and atorvastatin, lisinopril and hydrochlorothiazide, atorvastatin and clopidogrel, atorvastatin and metformin, metformin/lisinopril/atorvastatin, clopidogrel/atorvastatin/lisinopril, glipizide/metformin/lisinopril, atorvastatin/amlodipine/lisinopril, amlodipine/hydrochlorothiazide/lisinopril, carvedilol/atorvastatin/lisinopril, atorvastatin/metoprolol/lisinopril, clopidogrel/metoprolol/atorvastatin, lisinopril/carvedilol/furosemide, and amlodipine/metformin/lisinopril.

The present invention can also recommend alternate drugs of similar class (such as any of the classes described above) as an output 30 based on improving an efficacy-toxicity profile. For example, the logic engine can recommend using CRESTOR® (AstraZenica) instead of LIPITOR® (Pfizer), or ELOQUIS® (Bristol-Myers Squibb) instead of XARELTO® (Janssen). The output 30 can include information related to the efficacy-toxicity profile of each drug so that a medical professional can make an informed decision about what is best for the patient.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A computer-implemented method for dosing single and multiple drugs for an individual patient, by
 a healthcare professional collecting and inputting data from the individual patient including drugs to be taken by the patient into a database with a central artificial intelligence (AI) system stored on computer readable media,
 the central AI system analyzing the individual patient data in view of dosing criteria established based on outside patient data from clinical trial databases, electronic medical records, pharmaceutical companies, private databases, and contract research organizations (CROs), wherein outside patients experienced safety and efficacy, the central AI system creating features from data points of outside patient data variables that affect drug metabolism, the central AI system extracting all the features and creating a model using the features from the outside patient data variables relating dosing to patient condition of the outside patients and effect of drugs on the condition that affect efficacy and toxicity of all drugs taken by the individual patient, the variables including age of patient, weight of patient, known side effects of drugs alone and in combinations with other drugs with the outside patients, known toxicity range as related to median effective dose (ED 50) and dose response points, efficacy ranges, and chronic treatment effect versus acute treatment with outside patients, the central AI system identifying nearest neighbors of the outside patients having similar patient data and/or underwent a treatment plan with similar drug combinations to the individual patient and identifying related clinical trial data with a K-Nearest Neighbor algorithm, the central AI system employing a combination of artificial intelligence techniques, both supervised and unsupervised, including model logic of classifiers and expert rules that are prepopulated by practitioners and published research and are assigned a degree of truth, wherein the central AI system is unique to given inputs and is trained on demand to emphasize individuality of the individual patient and symptoms, the central AI system assigning confidence and weight to the individual patient data, the related clinical trial data, and the outside patient data variables, wherein patient data includes continuous values and discrete values, the central AI system using the classifiers and the expert rules implemented in series, the central AI system comparing the individual patient data to neighboring patient data with weighting schemes, the central AI system calculating the classifiers and model over the range of all doses considered by the model for the individual patient, wherein for each dosage, classifications with confidence intervals are calculated, the model is ran using the dosages mapped out to the classifiers, the outputs from the classifiers and the model are weighted and combined to determine an optimal dose for each drug, and the central AI system determining a dose or doses of the single or multiple drugs, respectively, for each drug taken by the individual patient and maximizing therapeutic effect while minimizing adverse effects for the combination of drugs taken, the central AI system producing clinical outputs of a recommended dosing range of the single or multiple drugs and in real time communication with a dispensing device to administer the drugs, and displaying the dose in a readable report for a practitioner.

2. The computer-implemented method of claim 1 wherein the individual patient data and the outside patient data is chosen from the group consisting of pharmacokinetics, distribution, prior toxicity and efficacy determinations, age, metabolism, and combinations thereof.

3. The computer-implemented method of claim 1 further including the step of dispensing the drugs to the individual patient in the determined doses.

4. A non-transitory computer-readable media including a computer-implemented algorithm for dosing single and multiple drugs for an individual patient, by collecting and inputting, data from the individual patient including drugs to be taken by the patient into a database with a central artificial intelligence (AI) system stored on non-transitory computer readable media, the central AI system analyzing the individual patient data using supervised and unsupervised AI techniques, in view of dosing criteria established based on outside patient data of from clinical trial data from outside databases of clinics, electronic medical records, pharmaceutical companies, private databases, and contract research organizations (CROs), wherein outside patients experienced safety and efficacy, the central AI system creating features from data points of outside patient data variables that affect drug metabolism, the central AI system extracting all the features and creating a model using the features from the outside patient data relating dosing to patient condition of the outside patients and effect of drugs on the condition that affect efficacy and toxicity of all drugs taken by the individual patient, wherein the variables include age of patient, weight of patient, known side effects of drugs alone and in combinations with other drugs with the outside patients, known toxicity range as related to median effective dose (ED 50) and dose response points, efficacy ranges, and chronic treatment effect versus acute treatment, the central AI system identifying nearest neighbors of the outside patients having similar patient data and/or underwent/undergoing a treatment plan with similar drug combinations to the individual patient and identifying related clinical trial data with a K-Nearest Neighbor algorithm, the central AI system employing the supervised and unsupervised AI techniques, including model logic of classifiers and expert rules that are prepopulated by practitioners and published research and are assigned a degree of truth, wherein the central AI system is unique to given inputs and is trained on demand to emphasize the individuality of the individual patient and symptoms, the central AI system assigning confidence and weight to the individual patient data, the related clinical trial data, and the outside patient data variables, wherein patient data includes continuous values and discrete values, the central AI system using the classifiers and the expert rules implemented in series, the central AI system comparing the individual patient data to neighboring patient data with weighting schemes, the central AI system calculating the classifiers and model over the range of all doses considered by the model for the individual patient, wherein for each dosage, classifications with confidence intervals are calculated, the model is ran using the dosages mapped out to the classifiers, the outputs from the classifiers and the model are weighted and combined to determine an optimal dose for each drug, and the central AI system determining a dose or doses of the single or multiple drugs, respectively, for each drug taken by the individual patient and maximizing therapeutic effect while minimizing adverse effects for the combination of drugs taken, the central AI system producing clinical outputs of a recommended dosing range of the single or multiple drugs in real time communication with a dispensing device to administer the drugs, and displaying the dose in a readable report for a practitioner.

5. The non-transitory computer-readable media including the computer-implemented algorithm of claim 4 wherein information flows from data input from the individual patient and the outside patient data to the central AI to and from a healthcare professional.

6. A computer-implemented logic engine for dosing multiple drugs, including an algorithm stored on non-transitory computer readable media for collecting outside data from outside databases of clinics, electronic medical records, pharmaceutical companies, private databases, and contract research organizations (CROs) to establish criteria for safely and efficaciously dosing multiple drugs to an individual patient and storing the outside data and individual patient data in a database, analyzing the patient data in view of criteria established from the clinical trial data with a central artificial intelligence (AI) system, the central AI system creating features from data points of outside patient data variables that affect drug metabolism, the central AI system extracting all the features and creating a model using the features from the outside patient data relating dosing to patient condition and effect of drugs on the condition affecting efficacy and toxicity of all drugs taken by the individual patient, wherein the variables include age of patient, weight of patient, known side effects of drugs alone and in combinations with other drugs with the outside patients, known toxicity range as related to median effective dose (ED 50) and dose response points, efficacy ranges, and chronic treatment effect versus acute treatment with outside patients, the central AI system identifying nearest neighbors of the outside patients having similar patient data and/or underwent/undergoing a treatment plan with similar drug combinations to the individual patient and identifying related clinical trial data with a K-Nearest Neighbor algorithm, the central AI system employing a combination of artificial intelligence techniques, both supervised and unsupervised, including model logic of classifiers and expert rules that are prepopulated by practitioners and published research and are assigned a degree of truth, wherein said logic engine is unique to given inputs and is trained on demand to emphasize the individuality of the individual patient and symptoms, the central AI system assigning confidence and weight to the individual patient data, the related clinical trial data, and the outside patient data variables, wherein patient data includes continuous values and discrete values, the central AI system using the classifiers and the expert rules implemented in series, the central AI system comparing the individual patient data to neighboring patient data with weighting schemes, the central AI system calculating the classifiers and model over the range of all doses considered by the model for the individual patient, wherein for each dosage, classifications with confidence intervals are calculated, the model is ran using the dosages mapped out to the classifiers, the outputs from the classifiers and the model are weighted and combined to determine an optimal dose for each drug, and determining a dose or doses of the single or multiple drugs, respectively, for each drug taken, maximizing therapeutic effect while minimizing adverse effects for the combination of drugs taken, producing clinical outputs of a recommended dosing range of the single or multiple drugs in real time communication with a dispensing device to administer the drugs, providing an output in the form of a practitioner readable report.

7. The computer-implemented logic engine of claim 6 wherein the individual patient data includes images chosen from the group consisting of computerized axial tomography (CAT) scans, CT scans, X-rays, magnetic resonance imaging (MRI), ultrasounds, and positron emission tomography (PET) scans.

8. The computer-implemented logic engine of claim 7 wherein the algorithm further performs the steps of analyzing reports from the images, encoding the reports using a natural language processing (NLP) algorithm to extract features, and informing the database of the features, along with structured findings from a radiologist.

\* \* \* \* \*